US008469985B2

(12) United States Patent
Nishiuchi (10) Patent No.: US 8,469,985 B2
(45) Date of Patent: *Jun. 25, 2013

(54) PUNCTURE INSTRUMENT

(75) Inventor: Daisuke Nishiuchi, Yamanashi (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/133,293

(22) PCT Filed: Nov. 12, 2009

(86) PCT No.: PCT/JP2009/069589
§ 371 (c)(1),
(2), (4) Date: Jun. 7, 2011

(87) PCT Pub. No.: WO2010/067695
PCT Pub. Date: Jun. 17, 2010

(65) Prior Publication Data
US 2011/0238101 A1    Sep. 29, 2011

(30) Foreign Application Priority Data

Dec. 8, 2008    (JP) .................................. 2008-312206

(51) Int. Cl.
    *A61B 17/32*    (2006.01)
(52) U.S. Cl.
    USPC ......................................... 606/181; 606/182
(58) Field of Classification Search
    USPC ............... 606/181, 182, 183, 185; 600/564, 600/566, 567, 573, 583; 604/22
    See application file for complete search history.

(56) References Cited

U.S. PATENT DOCUMENTS

| 4,892,097 | A | * | 1/1990 | Ranalletta et al. | 606/182 |
| 5,366,470 | A | * | 11/1994 | Ramel | 606/183 |
| 5,527,334 | A | * | 6/1996 | Kanner et al. | 606/182 |
| 6,945,982 | B2 | * | 9/2005 | Marshall et al. | 606/182 |
| 7,998,087 | B2 | | 8/2011 | Amano et al. | |

(Continued)

FOREIGN PATENT DOCUMENTS

| EP | 1 688 087 A1 | 8/2006 |
| JP | 2007-536008 A | 12/2007 |

(Continued)

OTHER PUBLICATIONS

International Search Report (PCT/ISA/210) issued on Jun. 15, 2010, by European Patent Office as the International Searching Authority for International Application No. PCT/JP2009/069589.

(Continued)

*Primary Examiner* — Ryan Severson
*Assistant Examiner* — Anh Dang
(74) *Attorney, Agent, or Firm* — Buchanan Ingersoll & Rooney PC (57) ABSTRACT

A puncture instrument includes a movable body movably disposed in a case, and a needle unit held by the movable body and having a needle. When a distal end face of the movable body is brought into abutment against a region to be punctured and the case is advanced toward the region to be punctured, the case is advanced together with the needle unit, and the tip end of the needle becomes protruded from the movable body and punctures the region to be punctured. An arm of the needle unit is abutted against and turned about a fulcrum member, thereby withdrawing the needle rearwardly.

9 Claims, 12 Drawing Sheets

U.S. PATENT DOCUMENTS

| | | |
|---|---|---|
| 8,221,335 B2 | 7/2012 | Amano et al. |
| 2002/0087180 A1 | 7/2002 | Searle et al. |
| 2004/0092997 A1 | 5/2004 | Levin et al. |
| 2006/0178686 A1 | 8/2006 | Schraga |
| 2006/0229651 A1* | 10/2006 | Marshall et al. ............... 606/181 |
| 2006/0264997 A1 | 11/2006 | Colonna et al. |
| 2007/0185515 A1* | 8/2007 | Stout .............................. 606/181 |
| 2008/0147107 A1* | 6/2008 | Roe et al. ....................... 606/181 |
| 2008/0243161 A1 | 10/2008 | Abulhaj |

FOREIGN PATENT DOCUMENTS

| | | |
|---|---|---|
| JP | 2008-99999 A | 5/2008 |
| WO | 03/049613 A1 | 6/2003 |
| WO | WO 2004/039429 A2 | 5/2004 |
| WO | WO 2005/110227 A1 | 11/2005 |
| WO | 2007/088905 A1 | 8/2007 |
| WO | 2008/009985 A1 | 1/2008 |

OTHER PUBLICATIONS

Written Opinion (PCT/ISA/237) issued on Jun. 15, 2010, by European Patent Office as the International Searching Authority for International Application No. PCT/JP2009/069589.

Japanese Office Action issued Apr. 23, 2013 by the Japanese Patent Office in corresponding Japanese Application No. 2008-312206, and partial English translation of Office Action (4 pgs).

Chinese Office Action issued Mar. 14, 2013 by the Chinese Patent Office in corresponding Chinese Application No. 200980149282.9, and partial English translation (of Office Action 10 pgs).

* cited by examiner

PUNCTURE INSTRUMENT

TECHNICAL FIELD

The present invention relates to a puncture instrument for instantaneously projecting a needle to puncture the skin of a patient.

BACKGROUND ART

It is recommended that diabetic patients perform a daily self-management of diabetes by measuring blood sugar level variations by themselves. For the purpose of the measuring, there has been put to practical use a blood component measuring device. The blood component measuring device measures blood glucose levels by mounting a test paper impregnated with a reagent, which gives a color depending on the amount of glucose in blood, applying blood to the test paper to cause the test paper to produce a color, and optically measuring the degree of the color for thereby determining and displaying the blood glucose level.

In order for a patient to sample his or her own blood, the patient uses a puncture instrument equipped with an axially movable needle. As disclosed in Japanese Laid-Open Patent Publication No. 2007-536008 (PCT) (WO2005/110227A1), for example, such a puncture instrument employs a drive spring for axially biasing the needle. When the drive spring expands from a compressed state, it causes the needle to project instantaneously and puncture the skin, e.g., a finger, a palm, an arm, or the like, of the patient, for thereby allowing a small amount of blood to flow out. After the skin is punctured, the needle is pulled from the skin and retracted into a housing by a return spring, which is separate from the drive spring.

SUMMARY OF INVENTION

According to the aforementioned background art, the puncture instrument requires a separate drive spring for axially biasing the needle, and a return spring for retracting the needle after puncturing the skin. The puncture instrument therefore is likely to be complex in structure and high in manufacturing cost.

It is a general object of the present invention to provide a puncture instrument, which is made inexpensive by simplifying its structure.

According to the present invention, there is provided a puncture instrument comprising:

a case;

a needle movably disposed in the case and having a sharp needle tip;

needle moving means for moving the needle toward a proximal end of the case; and an abutting member movably disposed in the case for abutment against the skin, the needle being movably held by the abutting member, wherein when the abutting member is moved toward the proximal end of the case, the needle tip is protruded from an end of the abutting member, and thereafter the needle is moved toward the proximal end to house the needle tip in the abutting member.

According to the invention, the puncture instrument does not require a resilient body to bias the needle assembly in a puncturing direction, while still allowing the needle to puncture the skin stably. Further, the puncture instrument is simple in structure. Since the puncture instrument is of a simple structure, the puncture instrument can be mass-produced and can be manufactured inexpensively.

According to the present invention, there is also provided a puncture instrument comprising:

a case;

a needle assembly movably disposed in the case and comprising a needle having a sharp needle tip and a hub holding the needle;

at least one arm having a first junction at one end thereof, joined to the hub by the first junction, and inclined from the first junction toward a proximal end of the case in an initial state;

a support rod joined to the arm by a second junction at another end of the arm, extending from the second junction toward a distal end of the case, and having a distal end to be fixed to the case; and an abutting member movably disposed in the case, the needle assembly being movably held by the abutting member, the abutting member having an abutting portion for abutment against the skin, a distal end opening formed in the abutting portion for protruding the needle tip therethrough, and a fulcrum member disposed on an opposite side to the distal end opening, wherein when the abutting member is moved toward the proximal end of the case, the needle tip is protruded from the distal end opening, and the fulcrum member abuts against the arm to cause the arm to turn about the fulcrum member, thereby causing the arm to be inclined from the first junction toward the distal end of the case, thereby to move the needle assembly toward the proximal end of the case to house the needle tip in the abutting member.

According to the present invention, when the abutting portion of the abutting member abuts against the skin and moves toward the proximal end of the case, the needle tip of the needle is protruded from the distal end opening of the abutting member and punctures the skin. The abutting member is further moved toward the proximal end, and the fulcrum member abuts against the arm to cause the arm to turn, whereby the needle assembly including the needle is moved toward the proximal end to house the needle tip in the abutting member.

Accordingly, the puncture instrument does not require a resilient body for biasing and discharging the needle assembly in a puncturing direction, while still allowing the needle to puncture the skin stably. Furthermore, the puncture instrument is simple in structure. Since the puncture instrument is of a simple structure, the puncture instrument can be mass-produced and can be manufactured inexpensively.

According to the present invention, there is also provided a puncture instrument comprising:

a case;

a needle assembly movably disposed in the case and comprising a needle having a sharp needle tip and a hub holding the needle;

an abutting member movably disposed in the case, the needle assembly being movably held by the abutting member, the abutting member having an abutting portion for abutment against the skin and a distal end opening formed in the abutting portion for protruding the needle tip therethrough;

a resilient member disposed between the needle assembly and the abutting member in the case, for biasing the needle assembly toward a proximal end of the case; and a releasing mechanism for releasing the needle assembly from a non-displaceable state, in which the needle assembly is not displaceable toward the proximal end, wherein when the abutting member is moved toward the proximal end, the needle tip is protruded from the distal end opening, and the abutting member causes the releasing mechanism to release the needle assembly from the non-displaceable state, for thereby moving the needle assembly toward the proximal end under the resiliency of the resilient member.

According to the present invention, when the abutting portion of the abutting member abuts against the skin and moves toward the proximal end, the needle tip of the needle is protruded from the distal end opening of the abutting member and punctures the skin. The abutting member is further moved toward the proximal end, and the releasing mechanism releases the needle assembly from a non-displaceable state, whereupon the needle assembly including the needle is withdrawn toward the proximal end under the resiliency of the resilient member.

Therefore, the puncture instrument does not require a resilient body to bias the needle assembly in a puncturing direction, while still allowing the needle to puncture the skin stably. Furthermore, the puncture instrument is simple in structure. Since the puncture instrument is of a simple structure, the puncture instrument can be mass-produced and can be manufactured inexpensively.

DESCRIPTION OF EMBODIMENTS

Figure 1:
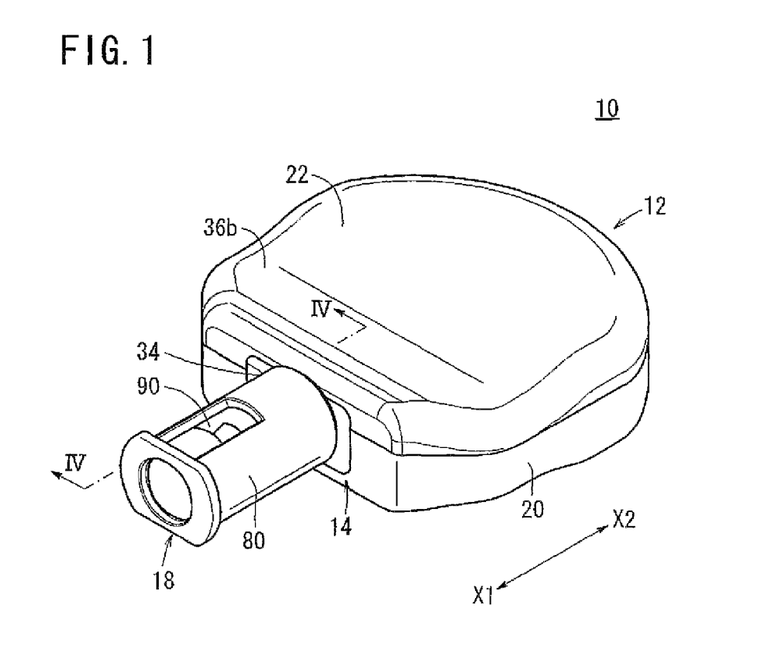
FIG. 1 is an external perspective view of a puncture instrument according to a first embodiment of the present invention.

In FIG. 1, reference numeral 10 denotes a puncture instrument according to a first embodiment of the present invention. The direction indicated by the arrow X1 in FIG. 1 points toward a front side (distal end) of the puncture instrument, whereas the direction indicated by the arrow X2 in FIG. 1 points toward a rear side (proximal end) of the puncture instrument.

Figure 2:
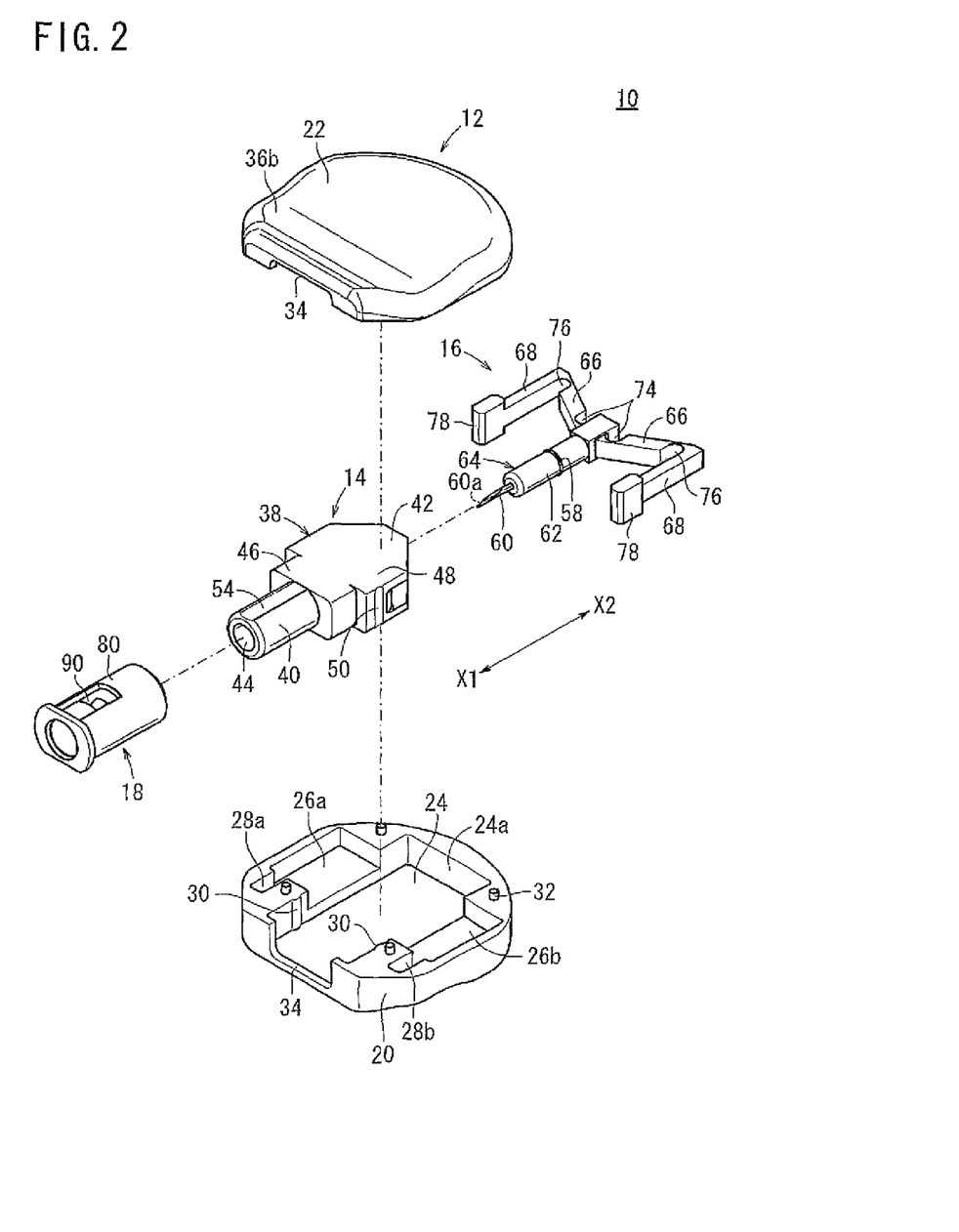
FIG. 2 is an exploded perspective view of the puncture instrument shown in FIG. 1.
Figure 3:
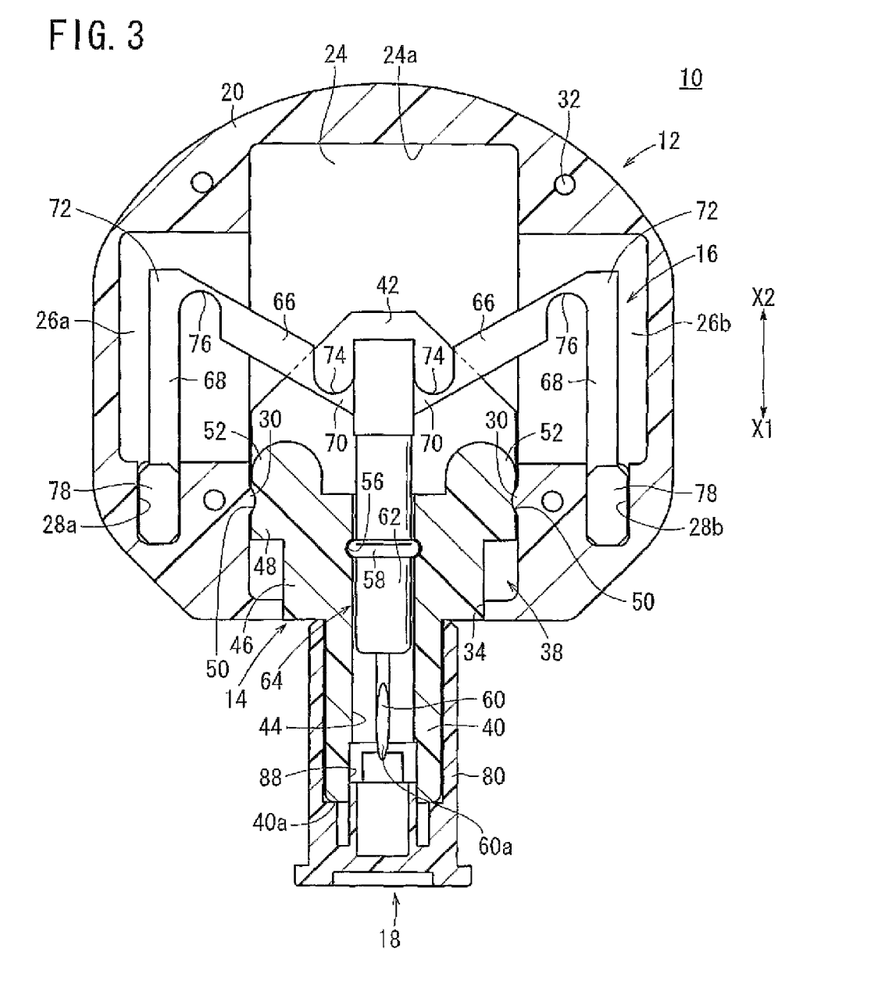
FIG. 3 is a longitudinal cross-sectional view of the puncture instrument with a protective cap mounted thereon.

As shown in FIGS. 1 to 3, the puncture instrument 10 comprises a case 12, a movable body (abutting member) 14 movably disposed in the case 12, a needle unit 16 held by the movable body 14, and a protective cap (cap) 18 mounted on an end of the movable body 14. The puncture instrument 10 can be made of resin (e.g., polypropylene or polyethylene) or metal, except for a needle 60 to be described later.

The case 12 is of a substantially circular shape and comprises a base member 20 and a cover member 22, which covers the base member 20.

The base member 20 is open on an upper surface thereof, and has a rectangular first space 24 formed substantially centrally therein. The movable body 14 and the needle unit 16 are movably disposed in the first space 24. The first space 24 extends from a front end toward a rear end of the case 12. The base member 20 has a pair of second spaces 26a, 26b formed on both side portions of the first space 24 for storing part of the needle unit 16 therein, and a pair of holding grooves 28a, 28b extending from ends of the second spaces 26a, 26b toward the front side (in the direction indicated by the arrow X1). The second spaces 26a, 26b and the holding grooves 28a, 28b are disposed symmetrically with respect to the first space 24, respectively.

A pair of ridges (first engaged portion) 30 having an arcuate cross section are disposed on respective left and right wall surfaces of the first space 24 near an opening 34, which shall be described later. The ridges 30 are disposed so as to face each other.

A plurality of pins 32 project from an upper surface of the base member 20 toward the cover member 22. More specifically, the pins 32 are located at positions on the front side (in the direction indicated by the arrow X1) and the rear side (in the direction indicated by the arrow X2) of the second spaces 26a, 26b.

The cover member 22 is thinner than the base member 20. When the movable body 14 and the needle unit 16 are housed in the base member 20, the cover member 22 is mounted on the base member 20 so as to cover the open upper surface thereof. When the cover member 22 is mounted on the upper surface of the base member 20, the pins 32 of the base member 20 are inserted respectively into holes (not shown) formed in the cover member 22. The cover member 22 is fixed integrally to the base member 20 by ultrasonic welding, for example, whereby the base member 20 and the cover member 22 jointly make up the case 12. The case 12 has a rectangular opening 34 formed in the distal end thereof. The movable body 14 includes a portion thereof that is inserted through the opening 34.

The case 12 has grip regions 36a, 36b on the surface thereof, which extend perpendicularly to an axis that interconnects the front and rear ends of the case 12. The grip regions 36a, 36b are formed as recesses having arcuate cross sections to allow the operator to grip the case 12 easily with the fingers F1, F2, and are located in symmetrical positions with respect to the base member 20 and the cover member 22 (see FIG. 5).

The movable body 14, which is disposed in the first space 24 inside the case 12, includes a main body 38, an abutment 40 projecting from a front end of the main body 38, and a pair of flanges (stoppers) 42 projecting from a rear end of the main body 38. A hub passage 44 penetrates linearly through the main body 38 and the abutment 40.

The main body 38 is in the form of a block and includes a narrow portion 46 disposed on a front side thereof (in the direction indicated by the arrow X1), which is inserted into the opening 34 in the case 12 in an initial state, and a wide portion 48 disposed on a rear side thereof (in the direction indicated by the arrow X2), which is wider than the narrow portion 46. The wide portion 48 has opposite side surfaces held in sliding contact with opposite wall surfaces of the first space 24, and a pair of recesses (first engaging portion) 50, which engages with the ridges 30 of the case 12 in the initial state.

The wide portion 48 also has fulcrum members 52 with semicircular cross sections on a rear end surface of the wide portion 48, which are disposed in positions on opposite sides centering around the hub passage 44. The paired fulcrum members 52 project rearwardly of the main body 38.

The flanges 42, in the form of substantially trapezoidal plates, extend rearwardly from upper and lower surfaces of the wide portion 48 in a progressively tapered configuration, and are spaced a predetermined distance from each other so as to face each other. The fulcrum members 52 are disposed between one and the other of the flanges 42.

The flanges 42 have flat rear ends lying perpendicular to the axis of the movable body 14. When the movable body 14 moves rearwardly (in the direction indicated by the arrow X2), the flanges 42 abut against a rear wall 24a of the first space 24 in order to prevent the movable body 14 from moving further. The flanges 42 thus function as stoppers for limiting movement of the movable body 14 in the rearward direction (the direction indicated by the arrow X2).

The abutment 40 has a substantially circular cross-sectional shape and a constant diameter. When the puncture instrument 10 punctures a patient, a distal end face (abutting portion) 40a of the abutment 40 abuts against the skin S of the patient (see FIG. 6). The hub passage 44, which penetrates through the abutment 40, includes a wider portion (distal end opening) 88 near the distal end face 40a thereof.

The abutment 40 has a pair of flat surfaces 54 (see FIG. 2) on an outer circumferential surface, which are formed flatwise parallel to the axis of the abutment 40. When the protective cap 18 is mounted on the abutment 40, the flat surfaces 54 abut against the inner circumferential surface of the protective cap 18, and serve as stops for preventing the protective cap 18 from rotating on the abutment 40.

The hub passage 44 includes an annular groove (second engaged portion) 56 formed in an inner circumferential surface thereof for engagement with an annular rib (second engaging portion) 58 of the needle unit 16, to be described below. The annular groove 56 with the annular rib 58 engaging therein provides a hermetic seal between the hub passage 44 and a needle assembly 64, thus preventing atmospheric air from being introduced from the first space 24 toward the needle 60 (in the direction indicated by the arrow X1).

The needle unit 16 comprises the needle assembly 64, which includes the needle 60 having a sharp needle tip 60a and a hub 62 for holding the needle 60, and a pair of arms 66 and rods 68, which are disposed symmetrically with respect to the axis of the needle assembly 64.

The needle unit 16 includes two arms 66 and two rods 68, which are simple in structure, have a symmetrical construction, and are well balanced. The needle unit 16 need not necessarily include two arms 66 and two rods 68, but may include one arm 66 and one rod 68, or three or more arms 66 and three or more rods 68. If there are three or more arms 66 and three or more rods 68, then the arms 66 and rods 68 may be arranged so as to surround the needle assembly 64 at equal angular intervals around the axis of the needle assembly 64.

The needle 60 comprises a hollow needle or a solid needle, which is made of a metal such as stainless steel, aluminum, or titanium, or a hard synthetic resin such as polyphenylene sulfide. The needle 60 is integrally fixed to the hub 62 by adhesive bonding, fusion, insert molding, or the like.

Each of the arms 66 is connected to the hub 62 by a first junction 70 at one end thereof, and also is connected to the proximal end of the rod 68 by a second junction 72 at the other end thereof. In the initial state, each of the arms 66 is spread rearwardly toward the left or right, and is inclined in a direction away from the axis of the hub 62. Stated otherwise, each of the arms 66 is inclined such that the second junction 72 is positioned rearwardly of the first junction 70 (in the direction indicated by the arrow X2) in the initial state.

The arms 66 have respective recesses 74 formed therein behind the first junctions 70 (in the direction indicated by the arrow X2), and respective recesses 76 formed therein in front of the second junctions 72 (in the direction indicated by the arrow X1). Therefore, the first junctions 70 and the second junctions 72 are narrower than the rest of the arms 66.

The rods 68 have a sufficient strength that is capable of supporting the arms 66, and are appropriately elastic so as to be bendable outwardly and function as leaf springs. The rods 68 have holders 78 disposed on distal ends thereof. The holders 78 are fixedly mounted in respective holding grooves 28a, 28b formed in the case 12, and the rods 68 are housed in the second spaces 26a, 26b. The rods 68 extend rearwardly from the distal ends thereof substantially parallel to the axis, and have proximal ends joined to the second junctions 72 of the arms 66.

In addition, appropriate gaps are provided between the rods 68 and the wall surfaces of the second spaces 26a, 26b. The arms 66 and the rods 68 jointly make up a needle withdrawing means (needle moving means).

The protective cap 18, which has a bottomed tubular shape, includes an outer tube 80 disposed on an outer circumferential side thereof and having an open rear end, the outer tube 80 being mounted on an outer circumferential surface of the abutment 40 of the movable body 14 so as to cover the abutment 40, and an inner tube 82 disposed in the outer tube 80 and fitted in an open end of the hub passage 44. The hub passage 44 is closed by the inner tube 82.

When the protective cap 18 is mounted on the movable body 14 disposed in the case 12, an end of the outer tube 80 abuts against the end face of the narrow portion 46 of the movable body 14. At this time, the end of the outer tube 80 includes portions held in abutment with the base member 20 and the cover member 22. Accordingly, even when external forces toward the proximal end of the protective cap 18 are applied to the protective cap 18, the protective cap 18 is not moved, and the abutment 40 is not pushed inadvertently.

Figure 4:
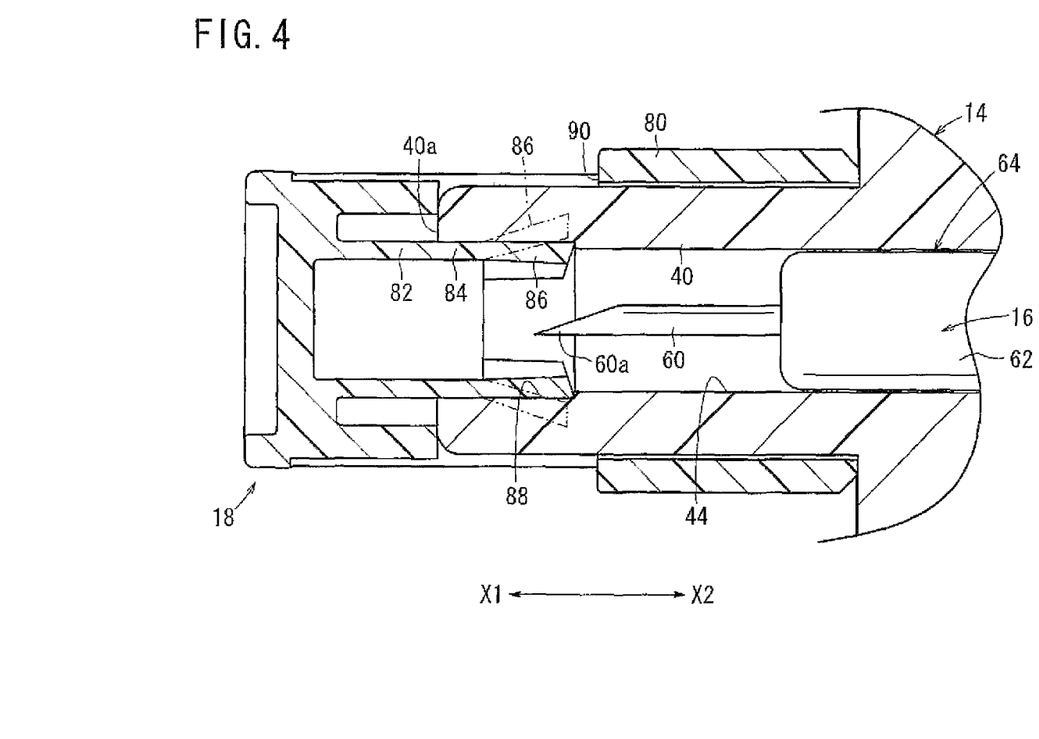
FIG. 4 is a cross-sectional view taken along line IV-IV of FIG. 1.

As shown in FIG. 4, the inner tube 82 has a pair of teeth 86 disposed on an end 84 thereof, which are spread rearwardly. When the inner tube 82 is inserted into the hub passage 44, the teeth 86 are bent toward the central axis and are inserted into the wider portion 88 of the hub passage 44.

The outer tube 80 that faces the teeth 86 has a pair of open windows 90 formed therein. When the protective cap 18 is mounted on the movable body 14, the assembly is irradiated with γ rays, an electron beam, or the like to sterilize the needle 60 housed in the movable body 14. The needle 60 is kept sterilized due to the hub passage 44 being hermetically sealed, since the end 84 of the inner tube 82 is fitted into the wider portion 88, and the annular rib 58 of the hub 62 engages within the annular groove 56 of the movable body 14. Since the teeth 86 are spread radially when the protective cap 18 is removed from the puncture instrument 10, the teeth 86 prevent the protective cap 18 from becoming mounted again, thereby reducing the danger of reusing by mistake a puncture instrument 10 that has already been used.

The puncture instrument 10 according to the first embodiment of the present invention is basically constituted as described above. Operations and advantages of the puncture instrument 10 will be described below. It is assumed that a fingertip of the patient is punctured by the puncture instrument 10.

Figure 5:
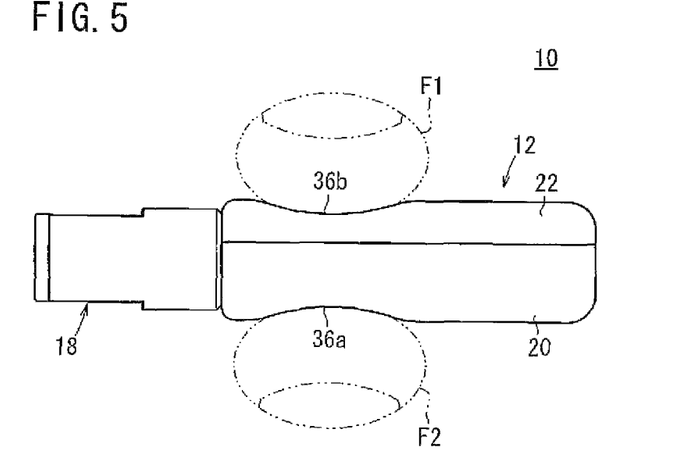
FIG. 5 is a side elevational view of the puncture instrument, with grip regions of a case being gripped by fingers.
Figure 6:
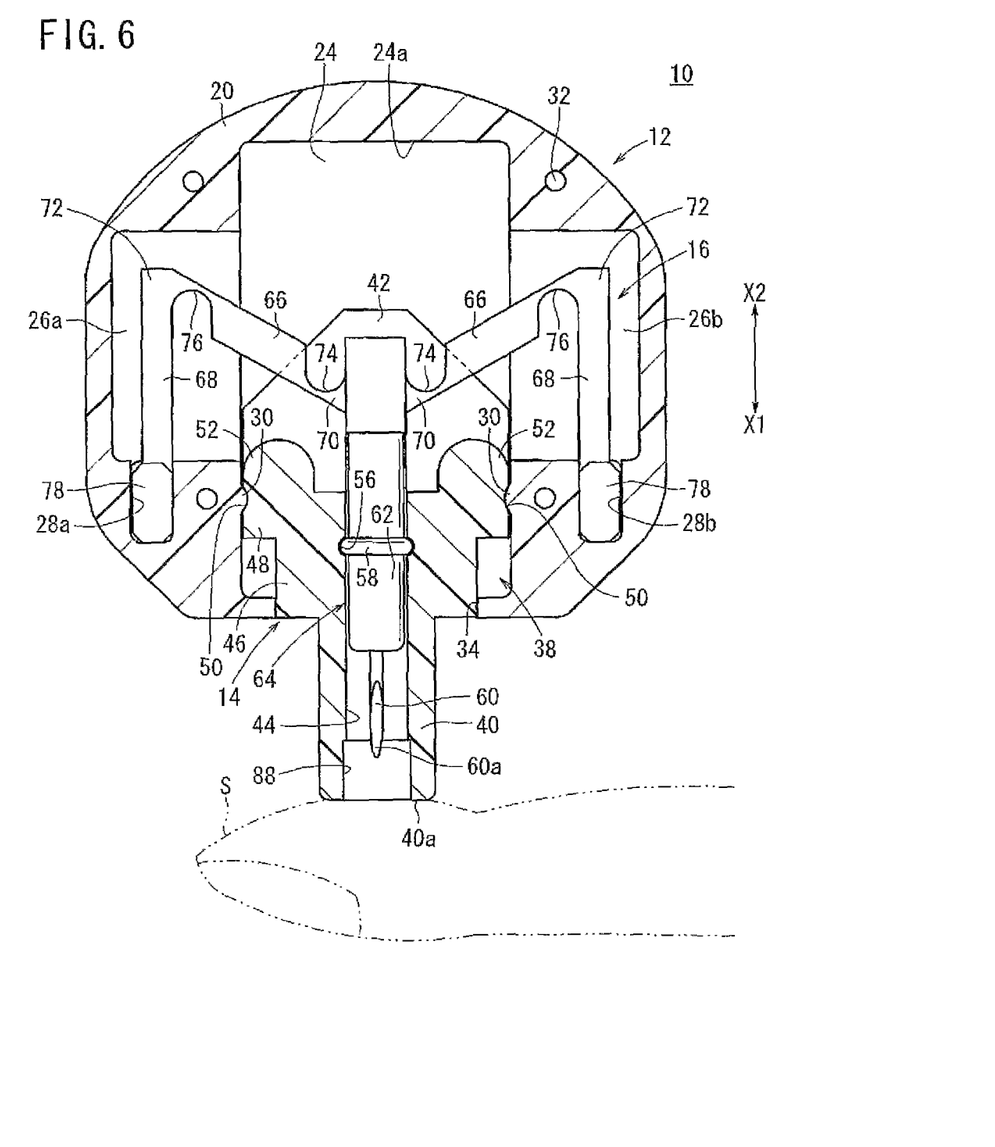
FIG. 6 is a cross-sectional view of the puncture instrument, showing an initial state thereof, in which the protective cap is removed from the puncture instrument and the tip end face of a movable body is abutted against the skin.

The case 12 of the puncture instrument 10 shown in FIG. 5 is gripped by the thumb F1 and the index finger F2, for example, and the protective cap 18 is removed from the movable body 14 (see FIG. 6). Thus, the puncture instrument 10 is placed in an initial state ready to perform a puncture operation. At this time as well, the puncture instrument 10 can reliably and stably be gripped by gripping the grip regions 36a, 36b on both surfaces of the case 12.

In the initial state of the puncture instrument 10 shown in FIG. 6, the distal end face 40a of the abutment 40 is brought into abutment against a fingertip (skin S) of the patient, and the case 12 is pushed toward the skin S (in the direction indicated by the arrow X1). When a predetermined load is applied to the case 12, while the abutment 40 of the movable body 14 is held in abutment with the skin S, the ridges 30 of the case 12 are released from the recesses 50 of the movable body 14, and only the case 12 is advanced relative to the movable body 14 toward the skin S of the patient (in the direction indicated by the arrow X1).

Stated otherwise, the movable body 14 is moved rearwardly relative to the case 12, so that the narrow portion 46 of the movable body 14 is housed in the case 12. At this time, since the needle unit 16 is held in the case 12 by the pair of arms 66 and the rods 68, the annular rib 58 is released from the annular groove 56 and moves together with the case 12.

More specifically, when a load directed toward the skin S is applied to the case 12 while the movable body 14 is held in abutment with the skin S, the movable body 14 and the needle unit 16 are released from a relatively non-displaceable state, which has been maintained by the annular rib 58 serving as the second engaging portion and the annular groove 56 serving as the second engaged portion, thus making the needle assembly 64 movable toward the distal end along the hub passage 44. Substantially at the same time, the recesses 50 serving as the first engaging portion and the ridges 30 serving as the first engaged portion are released from engagement with each other, thus making the case 12 and the movable body 14 relatively displaceable. A force, which is applied to release the annular rib 58 on the needle assembly 64 and the annular groove 56 in the movable body 14 from engagement with each other, is set to a level smaller than the force applied to release the recesses 50 in the movable body 14 and the ridges 30 on the case 12 from engagement with each other, as well as the force required to turn the arms 66.

Thus, when the case 12 is pushed toward the skin S to move the movable body 14 relatively toward the proximal end (in the direction indicated by the arrow X2), the needle assembly 64 is reliably released from engagement with the movable body 14, whereupon the movable body 14 is released from engagement with the case 12, and the arms 66 are turned to move the needle assembly 64 in a direction to withdraw the same. Since the engaging and engaged portions require relatively large forces to be released from engagement with each other, the needle tip 60a can subsequently be projected and withdrawn at a desired speed.

Figure 7:
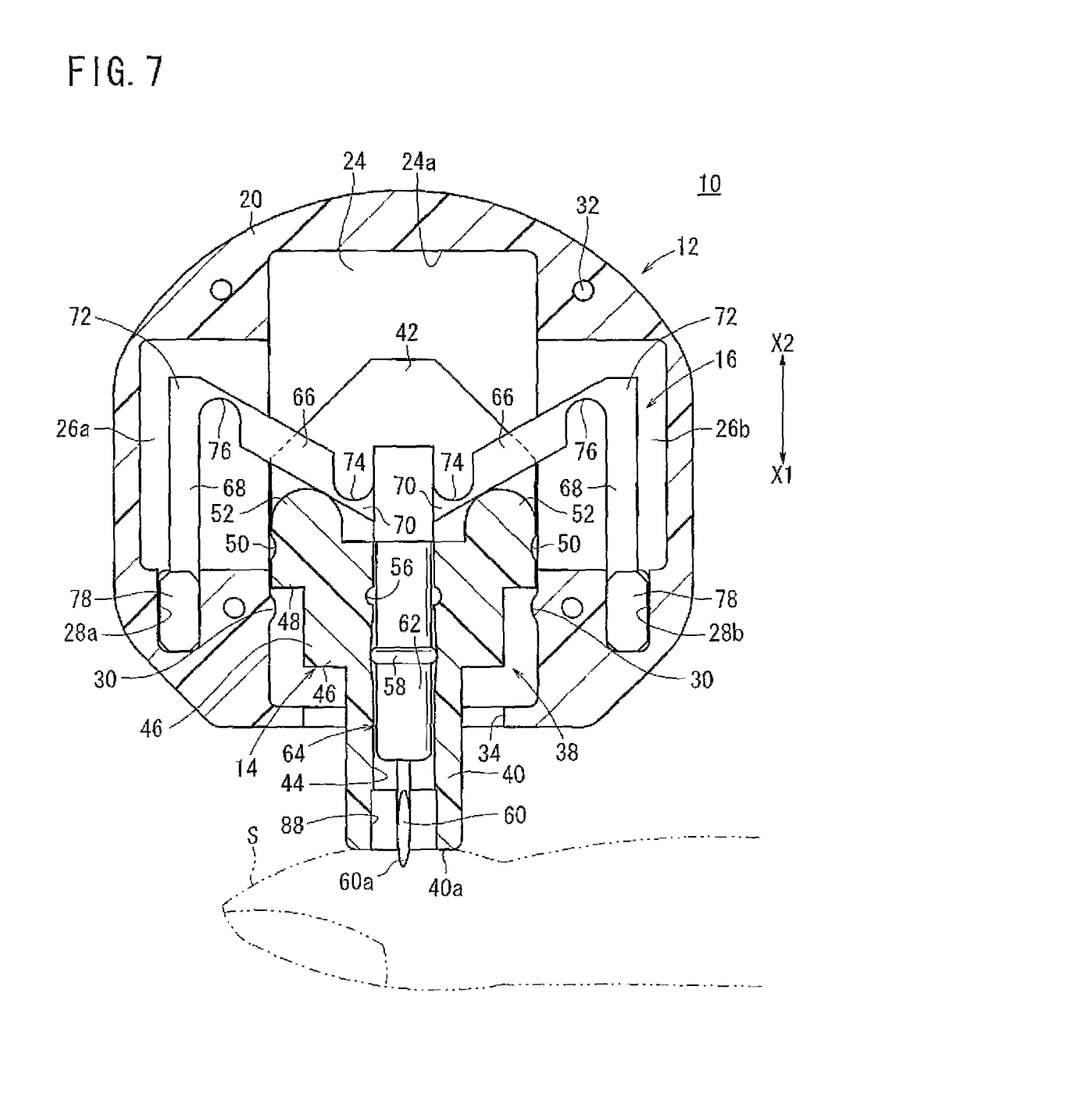
FIG. 7 is a cross-sectional view of the puncture instrument, showing a puncture state thereof, in which the case is moved toward the skin and a needle punctures the skin.

As shown in FIG. 7, while the case 12 is advanced, the tip end of the needle 60 of the needle assembly 64 projects through the opening 34 of the hub passage 44 from the distal end face 40a and punctures the skin S. The puncture instrument 10 does not require a resilient body to bias the needle assembly 64 axially, but rather, the needle tip 60a is directly pushed out of the hub passage 44 in the movable body 14 due to the relative displacement of the case 12 and the movable body 14, thereby stably puncturing the skin S. The length by which the needle 60 projects is limited, because the fulcrum members 52 abut against the arms 66 and serve as stoppers, so that the skin S can be punctured at an appropriate depth.

Figure 8:
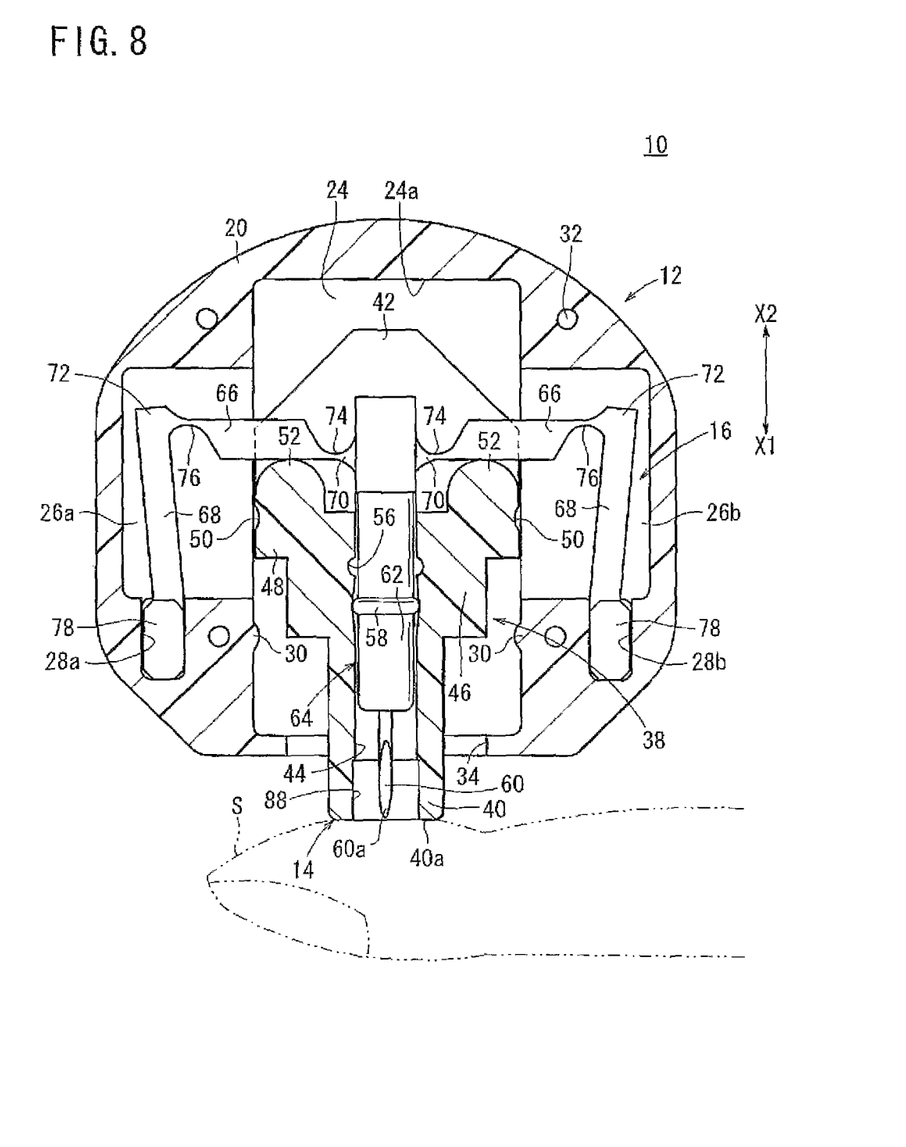
FIG. 8 is a cross-sectional view of the puncture instrument, showing a state thereof in which arms are turned about fulcrum members and the needle starts being retracted, following the puncture state of FIG. 7.

As shown in FIG. 8, when the case 12 is further advanced toward the skin S (in the direction indicated by the arrow X1) while the distal end face 40a of the movable body 14 is held in abutment with the skin S, the movable body 14 is further retracted relatively, thus causing the fulcrum members 52 to push the arms 66 upwardly and to turn the arms 66 about the second junctions 72. The needle assembly 64, which is joined to the first junctions 70 of the arms 66, is withdrawn and retracted along the hub passage 44, thereby allowing the tip end of the needle 60 to be housed inside the hub passage 44.

When the arms 66 are turned, since stresses are concentrated on the first junctions 70 and the second junctions 72, which are narrow, the first junctions 70 and the second junctions 72 become plastically deformed out of their elastic range, and rear portions of the rods 68 (in the direction indicated by the arrow X2) near the arms 66 are elastically deformed, so as to be pushed toward the side walls of the second spaces 26a, 26b.

Figure 9:
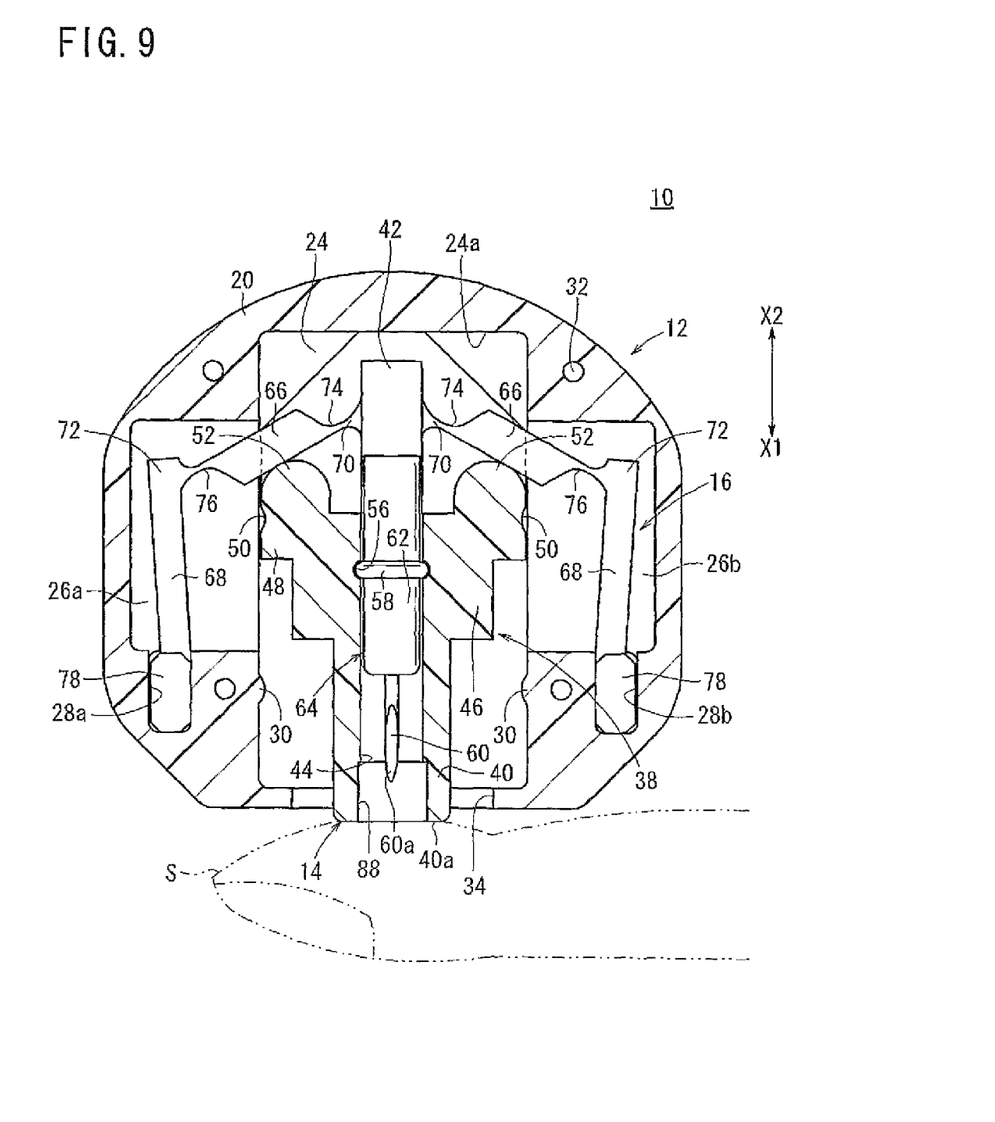
FIG. 9 is a cross-sectional view of the puncture instrument, showing a state thereof in which the needle is fully moved backwards to complete the puncture process.

As shown in FIG. 9, when the case 12 is further advanced toward the skin S (in the direction indicated by the arrow X1) while the distal end face 40a of the movable body 14 is held in abutment with the skin S, the arms 66 are further pushed upwardly by the fulcrum members 52 and turned about portions thereof which are abutted against the fulcrum members 52, thereby further retracting the needle assembly 64 along the hub passage 44. Finally, the flanges 42 of the movable body 14 abut against the rear wall 24a of the first space 24, whereupon the case 12 is prevented from being displaced relatively to the movable body 14. The puncture process is thus completed.

At this time, since the first junctions 70 and the second junctions 72 of the arms 66 have been turned and plastically deformed as a result of being pushed by the movable body 14, the elastic forces thereof are considerably lowered, and the first and second junctions 70, 72 exhibit almost no forces that act to return the arms 66 to their original attitude. That is, almost no forces act to push the needle assembly 64 forwardly. Therefore, the needle assembly 64 is not advanced again, but is held in a housed state within the case 12, so that the puncture instrument 10 is prevented from being reused.

The puncture process shown in FIGS. 6 to 9 is performed within a remarkably short period of time, and the tip end of the needle 60 projects from the distal end face 40a instantaneously.

When the skin S is simply punctured by the needle 60 in this manner, a small amount of blood flows out of the skin S and is sampled. The sampled blood is analyzed by a blood glucose meter or the like to measure blood components. The puncture instrument 10 is discarded after use. Since the needle 60 is fully inserted in the hub passage 44, there is no danger of the needle 60 being touched by someone when the puncture instrument 10 is discarded.

According to the first embodiment, as described above, the puncture instrument 10 does not incorporate therein a resilient body that biases the needle assembly 64 in the puncturing direction (in the axial direction). Instead, the needle assembly 64 is directly pushed out by the arms 66 and the rods 68, thereby causing the needle 60 to puncture the skin S stably. In addition, the puncture instrument 10 has a simple structure.

Since the puncture instrument 10 having such a simple structure can be mass-produced, the puncture instrument 10 is inexpensive and suitable for use as a disposable product. The puncture instrument 10 is basically made up of four components, i.e., the case 12, the movable body 14, the needle unit 16, and the protective cap 18. Therefore, the puncture instrument 10 is made up of a small number of parts, is simple in structure, and can easily be assembled.

The ridges 30 on the case 12 and the corresponding recesses 50 in the movable body 14 may be switched around.

In the first embodiment, as described above, the base member 20 and the cover member 22 are joined to form the case 12. However, the present invention is not limited to such a structure. Instead, the base member 20 and the cover member 22 may be of an integrated shape openably and closably coupled together by a hinge or the like. In such a case, the number of parts making up the case is reduced, and the work of assembling becomes easier.

Figure 10:
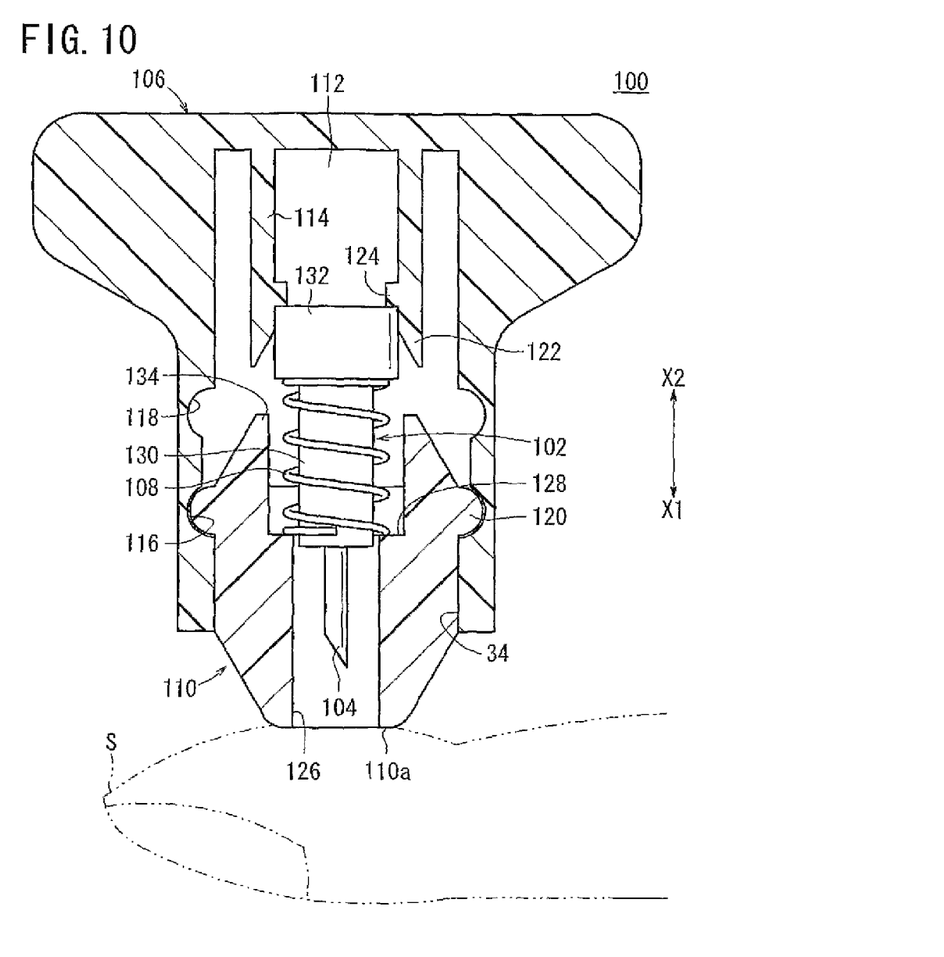
FIG. 10 is an overall longitudinal cross-sectional view of a puncture instrument according to a second embodiment of the present invention.
Figure 11:
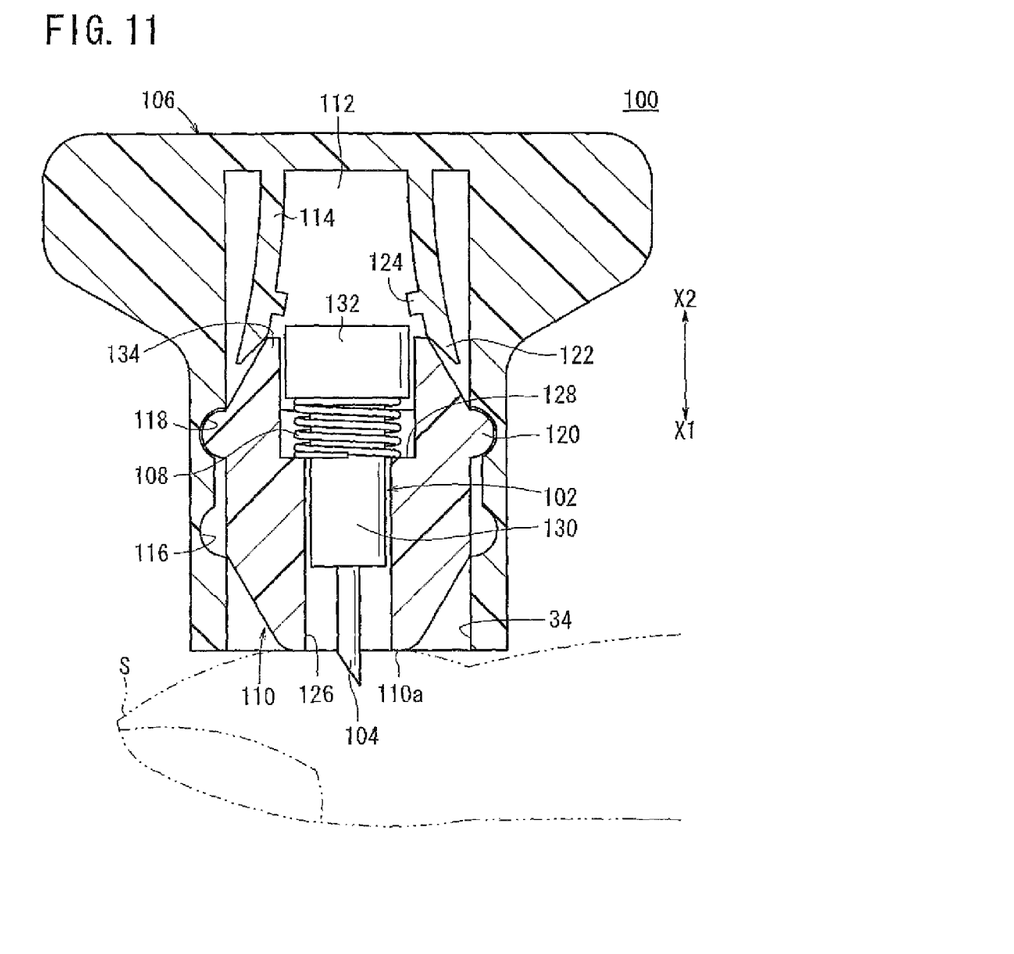
FIG. 11 is a cross-sectional view of the puncture instrument, showing a puncture state thereof, in which the skin is punctured by a needle of the puncture instrument shown in FIG. 10.
Figure 12:
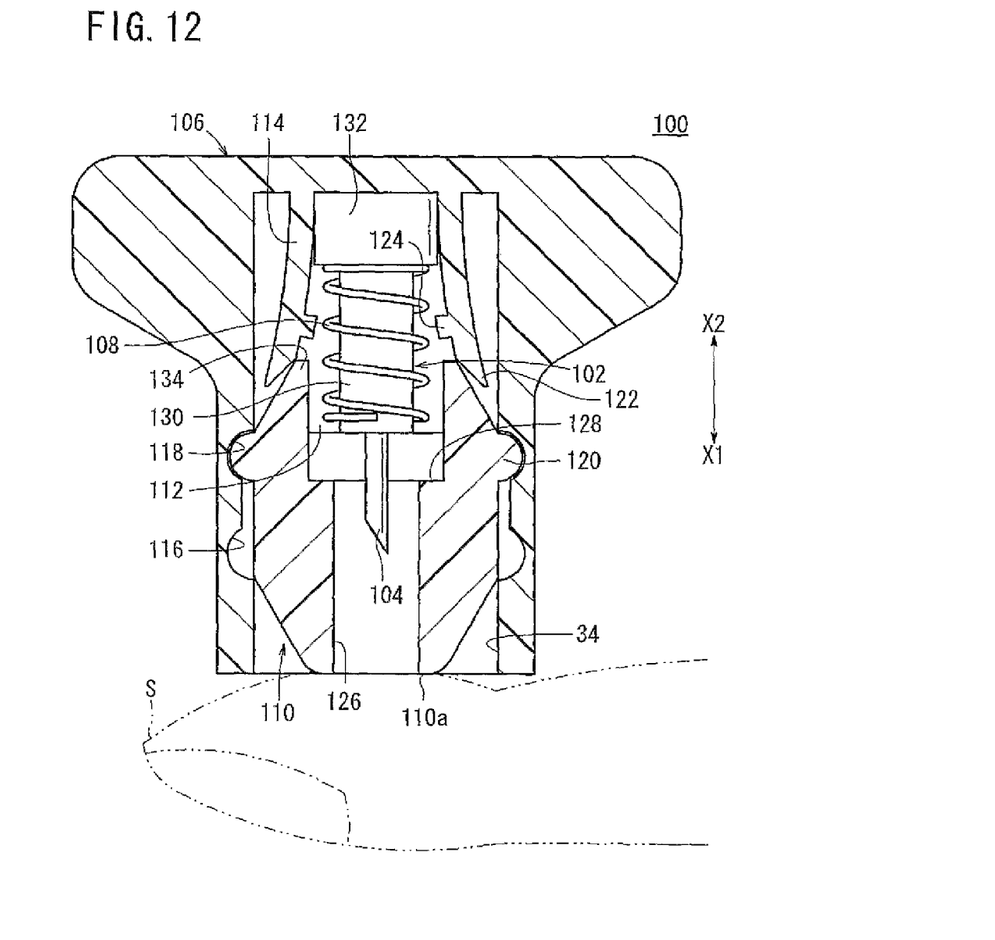
FIG. 12 is a cross-sectional view of the puncture instrument, showing a state thereof in which a moving member shown in FIG. 11 is retracted to complete the puncture process.

A puncture instrument 100 according to a second embodiment is shown in FIGS. 10 to 12. Those components of the puncture instrument 100, which are identical to those of the puncture instrument 10 according to the first embodiment, are denoted by identical reference characters, and descriptions about such components will be omitted in detail below.

As shown in FIGS. 10 to 12, the puncture instrument 100 according to the second embodiment differs from the puncture instrument 10 according to the first embodiment, in that the puncture instrument 100 includes a spring (resilient member) 108 that serves as a needle withdrawing means (needle moving means) for retracting a needle assembly 102 into a case 106, after the skin has been punctured by the needle 104 constituting the needle assembly 102.

The puncture instrument 100 includes a case 106, a movable body (abutting member) 110 movably disposed in the case 106, a needle assembly 102 held by the movable body 110, and a spring 108 for retracting the needle assembly 102 into the case 106.

The case 106 is substantially T-shaped and has a space 112 formed therein, which is open toward a distal end thereof (in the direction indicated by the arrow X1). The case 106 also includes a hollow cylindrical hub holder 114 disposed in the space 112 and having a plurality of slits formed in a rear end thereof (in the direction indicated by the arrow X2) for holding the rear end of the needle assembly 102. The space 112 has an inner wall surface, which has first and second recesses 116, 118 having semicircular cross sections formed therein. Ridges 120 disposed on side walls of the movable body 110 are capable of engagement with the first recess 116 and the second recess 118. The first and second recesses 116, 118 are spaced apart from each other by a predetermined distance in the axial direction of the case 106, the first recess 116 being positioned closer to the distal end of the case 106 (in the direction indicated by the arrow X1).

The hub holder 114 has a guide 122 disposed on a distal end thereof, which faces the movable body 110. The guide 122 has an inner circumferential surface progressively smaller in diameter toward the rear end thereof (in the direction indicated by the arrow X2). The hub holder 114 has a step 124 for engagement with the rear end of the needle assembly 102. The step 124 is disposed annularly on the inner circumferential surface of the hub holder 114, and projects radially-inwardly.

The movable body 110 is in the form of a hollow tube, and has opposite ends tapered such that the ends become progressively smaller in diameter toward distal ends thereof. The movable body 110 has a rear end 134 for contacting the hub holder 114 to release the needle assembly 102 out of a non-displaceable state. The movable body 110 has the pair of ridges 120 disposed on opposite side walls thereof for engaging either the first recess 116 or the second recess 118. In an initial state of the puncture instrument 100, as shown in FIG. 10, the ridges 120 engage within the first recess 116, and the distal end of the puncture instrument 100 projects out of the opening 34 in the case 106.

A hub passage 126 penetrates axially through the movable body 110. A spring hole 128 is formed in a rear end (in the direction indicated by the arrow X2) of the hub passage 126, and has a diameter that is greater than the distal end (in the direction indicated by the arrow X1) of the hub passage 126.

The needle assembly 102 comprises a needle 104 and a hub 130 that holds the needle 104. A spring holder 132 is disposed on a rear end of the hub 130. The spring holder 132 has a diameter greater than the distal end of the hub 130, which holds the needle 104. The distal end of the needle assembly 102 is inserted into the hub passage 126. The spring holder 132 is capable of being inserted into the spring hole 128.

In the initial state, a rear end of the spring holder 132 is inserted into the hub holder 114 and is held by the inner circumferential surface of the guide 122 and the step 124. At this time, the needle assembly 102 is prevented from moving rearwardly (in the direction indicated by the arrow X2) by the hub holder 114.

A spring 108, which may comprise a coil spring for example, is interposed between the spring holder 132 of the needle assembly 102 and the end of the spring hole 128. The spring 108 biases the needle assembly 102 toward the rear end (in the direction indicated by the arrow X2) of the case 106.

A puncture process carried out by the puncture instrument 100 thus constituted will briefly be described below. In the initial state of the puncture process carried out by the puncture instrument 100, as shown in FIG. 10, the movable body 110 projects out of the opening 34 in the case 106, while the needle assembly 102 is retracted under the resilient force of the spring 108, with the spring holder 132 being locked by the hub holder 114 (i.e., the non-displaceable state).

The case 106 of the puncture instrument 100 in the initial state is gripped by a patient (not shown). After a distal end face 100a of the movable body 110 is held in abutment with the skin S (e.g., a fingertip) of the patient, the case 106 is pushed and advanced toward the skin S (in the direction indicated by the arrow X1). At this time, the movable body 110 is not advanced together with the case 106, because the distal end face 100a is held in abutment with the skin S.

The ridges 120 of the movable body 110 are released from the first recess 116 of the case 106, and the case 106 is advanced alone relatively to the movable body 110 toward the skin S (in the direction indicated by the arrow X1). Stated otherwise, the movable body 110 is retracted relatively to the case 106. At the same time, as the case 106 is advanced, the needle assembly 102, which is held by the hub holder 114, is pushed toward the skin S (in the direction indicated by the arrow X1) with compressing the spring 108.

Upon movement of the case 106, the ridges 120 of the movable body 110 engage within the second recess 118, and the tip end of the needle 104 of the needle assembly 102, which is pushed by the case 106, projects through the hub passage 126 from the distal end face 110a and punctures the skin S. At this time, the rear end 134 of the movable body 110 is inserted into the hub holder 114, thereby spreading the guide 122 radially-outwardly. The needle assembly 102 is released from the state (non-displaceable state) of being held by the hub holder 114. As a result, the needle assembly 102 is pushed and retracted under the resiliency of the spring 108, and becomes housed in the hub holder 114, which is increased in diameter by the movable body 110, whereupon the puncture process is completed.

The puncture instrument according to the present invention is not limited to the above embodiments, but may have various other arrangements without departing from the scope of the invention.

The invention claimed is:

1. A puncture instrument comprising:
   a case;
   a needle assembly movably disposed in the case and comprising a needle having a sharp needle tip and a hub holding the needle;
   at least one arm having a first junction at one end thereof, joined to the hub by the first junction, and inclined from the first junction toward a proximal end of the case in an initial state;
   a support rod joined to the arm by a second junction at another end of the arm, extending from the second junction toward a distal end of the case, and having a distal end to be fixed to the case; and
   an abutting member movably disposed in the case, the needle assembly being movably held by the abutting member, the abutting member having an abutting portion for abutment against the skin, a distal end opening formed in the abutting portion for protruding the needle tip therethrough, and a fulcrum member disposed on an opposite side to the distal end opening,
   wherein when the abutting member is moved toward the proximal end of the case, the needle tip is protruded from the distal end opening, and the fulcrum member abuts against the arm to cause the arm to turn about the fulcrum member, thereby causing the arm to be inclined from the first junction toward the distal end of the case, and thereby to move the needle assembly toward the proximal end of the case to house the needle tip in the abutting member.

2. The puncture instrument according to claim 1, wherein the support rod comprises a leaf spring and is elastically deformed by a force applied by the arm when the abutting member is moved toward the proximal end.

3. The puncture instrument according to claim 1, wherein the arm is inclined in a direction toward the proximal end and away from the hub in the initial state, and when the abutting member is pushed toward the proximal end, the arm is turned about the fulcrum member and inclined in a direction toward the distal end of the case and away from the hub.

4. The puncture instrument according to claim 1, wherein at least one of the first junction and the second junction is narrower than the arm, and is plastically deformed when the arm is turned and inclined in varying directions.

5. The puncture instrument according to claim 1, wherein the arm comprises two arms and the rod comprises two rods, the arms and the rods being disposed symmetrically with respect to a longitudinal axis of the hub.

6. The puncture instrument according to claim 1, wherein the abutting member has a first engaging portion in the form of a ridge or a recess, and the case has a first engaged portion for engaging the first engaging portion when the abutting member is in the initial state.

7. The puncture instrument according to claim 6, wherein the abutting member has a second engaging portion in the form of a rib or a groove, and the hub has a second engaged portion for engaging the second engaging portion when the abutting member is in the initial state; and
   a force for releasing the second engaging portion and the second engaged portion out of engagement with each other is smaller than a force for releasing the first engaging portion and the first engaged portion out of engagement with each other, and is smaller than a force required to turn the arm.

8. The puncture instrument according to claim 1, further comprising:
   a cap removably mounted on the puncture instrument so as to cover a portion of the abutting member, which is protruded from the case,
   wherein the cap has an end abutting against a portion of the case for thereby preventing an external force from being applied to the abutting member.

9. The puncture instrument according to claim 1, wherein the abutting member has a stopper for abutting against an inner surface of the case to prevent the abutting member from moving when the abutting member is moved toward the proximal end.

* * * * *